United States Patent
Corr et al.

(10) Patent No.: US 10,959,965 B2
(45) Date of Patent: Mar. 30, 2021

(54) COMPOSITION COMPRISING SALBUTAMOL SULPHATE

(71) Applicant: MEXICHEM AMANCO HOLDING S.A. DE C.V., Estado de Mexico (MX)

(72) Inventors: Stuart Corr, Cheshire (GB); Timothy James Noakes, Flintshire (GB)

(73) Assignee: Mexichem Amanco Holding S.A. de C.V., Tlalnepanthla (MX)

( * ) Notice: Subject to any disclaimer, the term of this patent is extended or adjusted under 35 U.S.C. 154(b) by 0 days.

(21) Appl. No.: 14/784,798

(22) PCT Filed: Apr. 17, 2014

(86) PCT No.: PCT/GB2014/051221
§ 371 (c)(1),
(2) Date: Oct. 15, 2015

(87) PCT Pub. No.: WO2014/170689
PCT Pub. Date: Oct. 23, 2014

(65) Prior Publication Data
US 2016/0058714 A1    Mar. 3, 2016

(30) Foreign Application Priority Data
Apr. 17, 2013 (GB) .................................... 1306984

(51) Int. Cl.
| A61K 31/137 | (2006.01) |
| A61K 9/00 | (2006.01) |
| A61M 15/00 | (2006.01) |
| A61K 9/12 | (2006.01) |

(52) U.S. Cl.
CPC ............ *A61K 31/137* (2013.01); *A61K 9/008* (2013.01); *A61K 9/124* (2013.01); *A61M 15/009* (2013.01)

(58) Field of Classification Search
CPC ...... A61K 31/137; A61K 9/124; A61K 9/008; A61M 15/009
See application file for complete search history.

(56) References Cited

U.S. PATENT DOCUMENTS

| 5,439,570 | A | 8/1995 | Purewal et al. |
| 6,103,266 | A | 8/2000 | Tapolsky et al. |
| 6,413,497 | B1 | 7/2002 | Weil et al. |
| 6,475,467 | B1 | 11/2002 | Keller et al. |
| 7,105,152 | B1 | 9/2006 | Schultz et al. |
| 9,114,164 | B2 | 8/2015 | Corr et al. |
| 2007/0183982 | A1* | 8/2007 | Berkel ................. A61K 9/0043 424/40 |
| 2007/0256685 | A1 | 11/2007 | Mueller-Walz |
| 2009/0092559 | A1* | 4/2009 | Hoelz ...................... A61K 9/12 424/45 |
| 2010/0329984 | A1* | 12/2010 | Weers .................. A61K 9/0073 424/9.1 |
| 2014/0230812 | A1 | 8/2014 | Corr et al. |
| 2014/0234229 | A1 | 8/2014 | Corr et al. |
| 2014/0286877 | A1 | 9/2014 | Corr et al. |

FOREIGN PATENT DOCUMENTS

| CN | 1296814 A | 5/2001 |
| CN | 1389202 A | 1/2003 |
| EP | 0 372 777 A1 | 6/1990 |
| EP | 0 653 204 A2 | 5/1995 |
| EP | 0 995 434 A2 | 4/2000 |
| EP | 2 072 051 A1 | 6/2009 |
| GB | 2 392 915 A | 3/2004 |
| WO | WO 91/11173 A1 | 8/1991 |
| WO | WO 93/11747 A1 | 6/1993 |
| WO | WO 96/19198 A1 | 9/1996 |
| WO | WO 96/32151 A1 | 10/1996 |
| WO | WO 99/16422 A1 | 4/1999 |
| WO | WO 99/65460 A2 | 12/1999 |
| WO | WO 01/43722 A2 | 6/2001 |
| WO | WO 2005/034911 A1 | 4/2005 |
| WO | WO 2005/034927 A2 | 4/2005 |
| WO | WO 2006/004646 A1 | 1/2006 |
| WO | WO 2007/020204 A2 | 2/2007 |
| WO | WO 2010/052466 A1 * | 5/2010 |
| WO | WO 2011/023734 A1 | 3/2011 |
| WO | WO 2012/156711 A1 | 11/2012 |
| WO | WO 2013/054135 A1 | 4/2013 |
| WO | WO 2013/054137 A1 | 4/2013 |

OTHER PUBLICATIONS

HFC-152a: retrived from internet: https://www.daikin.com/chm/products/pdfDown.php?url=pdf/tds/tds_hfc152a_e.pdf. retrieved on Sep. 29, 2017.*
Patent Cooperation Treaty International Search Report from corresponding application No. PCT/GB2014/051221, dated Jul. 28, 2014, 3 pgs.
Patent Cooperation Treaty Written Opinion of the International Preliminary Examining Authority from corresponding application No. PCT/GB2014/051221, dated Mar. 19, 2015, 5 pgs.

(Continued)

*Primary Examiner* — Hong Yu
(74) *Attorney, Agent, or Firm* — Brinks Gilson & Lione

(57) ABSTRACT

A pharmaceutical composition is described that is suitable for delivery from a pressurised container. The composition is preferably free of polar excipients and comprises: (a) a propellant component that consists essentially of 1,1-difluoroethane (R-152a); (b) a surfactant component that comprises at least one surfactant compound other than oleic acid; and (c) a drug component that consists of salbutamol sulphate. The pharmaceutical composition can be delivered using a metered dose inhaler (MDI).

24 Claims, No Drawings

(56) References Cited

OTHER PUBLICATIONS

Patent Cooperation Treaty Notification of Transmittal of the International Preliminary Report on Patentability from corresponding application No. PCT/GB2014/051221, dated Sep. 9, 2015, 6 pgs.
Machine Translation of Chinese Publication No. CN 1296814 A.
Machine Translation of Chinese Publication No. CN 1389202 A.
Noakes, Tim, "Medial aerosol propellants", Journal of Fluorine Chemistry, vol. 118, 2002, pp. 35-45.

\* cited by examiner

COMPOSITION COMPRISING SALBUTAMOL SULPHATE

CROSS-REFERENCE TO RELATED APPLICATIONS

This application is the U.S. National Phase under 35 U.S.C. § 371 of International Application No. PCT/GB2014/051221, filed Apr. 17, 2014, designating the United States and published in English on Oct. 23, 2014, as WO 2014/170689, which claims priority to United Kingdom Application No. 1306984.4, filed Apr. 17, 2013, each of which is incorporated by reference in its entirety.

FIELD

The present invention relates to a pharmaceutical composition comprising salbutamol sulphate, a propellant and a surfactant. The composition is suitable for delivering the salbutamol sulphate from a pressurised aerosol container using a metered dose inhaler (MDI).

BACKGROUND

MDIs are the most significant type of inhalation drug delivery system and are well known to those skilled in the art. They are designed to deliver, on demand, a discrete and accurate amount of a drug to the respiratory tract of a patient using a liquefied propellant in which the drug is dissolved, suspended or dispersed. The design and operation of MDIs is described in many standard textbooks and in the patent literature. They all comprise a pressurised container that holds the drug formulation, a nozzle and a valve assembly that is capable of dispensing a controlled quantity of the drug through the nozzle when it is activated. All of these components are typically located in a housing that is equipped with a mouth piece. The drug formulation will comprise a propellant, in which the drug is dissolved, suspended or dispersed, and may contain other materials such as polar excipients, surfactants and preservatives.

In order for a propellant to function satisfactorily in MDIs, it needs to have a number of properties. These include an appropriate boiling point and vapour pressure so that it can be liquefied in a closed container at room temperature but develop a high enough pressure when the MDI is activated to deliver the drug as an atomised formulation even at low ambient temperatures. Further, the propellant should be of low acute and chronic toxicity and have a high cardiac sensitisation threshold. It should have a high degree of chemical stability in contact with the drug, the container and the metallic and non-metallic components of the MDI device, and have a low propensity to extract low molecular weight substances from any elastomeric materials in the MDI device. The propellant should also be capable of maintaining the drug in a homogeneous solution, in a stable suspension or in a stable dispersion for a sufficient time to permit reproducible delivery of the drug in use. When the drug is in suspension in the propellant, the density of the liquid propellant is desirably similar to that of the solid drug in order to avoid rapid sinking or floating of the drug particles in the liquid. Finally, the propellant should not present a significant flammability risk to the patient in use. In particular, it should form a non-flammable or low flammability mixture when mixed with air in the respiratory tract.

Dichlorodifluoromethane (R-12) possesses a suitable combination of properties and was for many years the most widely used MDI propellant, often blended with trichlorofluoromethane (R-11). Due to international concern that fully and partially halogenated chlorofluorocarbons (CFCs), such as dichlorodifluoromethane and trichlorofluoromethane, were damaging the earth's protective ozone layer, many countries entered into an agreement, the Montreal Protocol, stipulating that their manufacture and use should be severely restricted and eventually phased out completely. Dichlorodifluoromethane and trichlorofluoromethane were phased out for refrigeration use in the 1990's, but are still used in small quantities in the MDI sector as a result of an essential use exemption in the Montreal Protocol.

1,1,1,2-tetrafluoroethane (R-134a) was introduced as a replacement refrigerant and MDI propellant for R-12. 1,1,1,2,3,3,3-heptafluoropropane (R-227ea) was also introduced as a replacement for dichlorotetrafluoroethane (R-114) in the MDI sector and is sometimes blended with R-134a for this application.

Although R-134a and R-227ea have low ozone depletion potentials (ODPs), they have global warming potentials (GWPs), 1430 and 3220 respectively, that are now considered to be too high by some regulatory bodies, especially for dispersive uses when they are released into the atmosphere.

One industrial area that has received particular attention recently has been the automotive air-conditioning sector where the use of R-134a has come under regulatory control as a result of the European F-Gas Regulations. Industry is developing a number of possible alternatives to R-134a in automotive air conditioning and other applications that have a low greenhouse warming potential (GWP) as well as a low ozone depletion potential (ODP). Many of these alternatives include hydrofluoropropenes, especially the tetrafluoropropenes, such as 2,3,3,3-tetrafluoropropene (R-1234yf) and 1,3,3,3-tetrafluoropropene (R-1234ze).

Although the proposed alternatives to R-134a have a low GWP, the toxicological status of many of the components, such as certain of the fluoropropenes, is unclear and they are unlikely to be acceptable for use in the MDI sector for many years, if at all.

There are also other problems with R-134a and R-227ea. Most pharmaceutical actives for treating respiratory disorders, such as asthma, tend not to dissolve well in either R-134a or R-227ea and have to be handled as suspensions in the propellant. Drug suspensions give rise to a number of problems, such as nozzle blockage, agglomeration and sedimentation, the latter problem making it essential to shake the MDI thoroughly before use to ensure that the drug is evenly distributed in the propellant. Furthermore, if the pharmaceutical active settles quickly following re-suspension in the propellant, as is often the case, then the propellant/drug composition must be delivered from the MDI shortly after shaking in order to ensure that the dose that is delivered contains an effective concentration of the pharmaceutical active.

The problem of poorly dissolving drugs has been addressed by including a polar excipient in the composition which either helps to dissolve the drug to form a solution or else enhances wetting of suspended drug particles to yield a better dispersed and more stable suspension. A preferred polar excipient is ethanol. However, the use of large amounts of ethanol can tend to result in a coarse spray having droplet sizes that are too large for acceptable penetration into the deep bronchiole passages of the lung. Further, high levels of ethanol can have unacceptable irritancy to the mouth and throat, especially with younger users. Clearly it would be advantageous to reduce the amount of ethanol that is required to produce an acceptable formulation. It would be better still if the use of ethanol could be avoided altogether.

Surfactants have also been included in some formulations that include drugs that are either insoluble or only sparingly soluble in the propellant, as these can also help to produce a more stable suspension. Unfortunately, many of the toxicologically acceptable surfactants have sufficient solubility in either R-134a or R-227ea. As a result, ethanol has been added to the composition, where it functions not only as a wetter but also as a solvent for the surfactant. It would be beneficial to find a propellant/surfactant combination that allows for sufficient surfactant to be dissolved in the propellant without the inclusion of a polar excipient such as ethanol or with reduced levels of such an excipient.

There is a need for a MDI aerosol formulation that has a reduced GWP in comparison with R-134a and R-227ea, that has acceptable flammability and toxicity performance, which forms stable suspensions and that has reduced irritancy.

SUMMARY

According to a first aspect of the present invention there is provided a pharmaceutical composition that is free of polar excipients, said composition comprising:
a propellant component consisting essentially of 1,1-difluoroethane (R-152a),
a surfactant component comprising at least one surfactant compound other than oleic acid; and
a drug component consisting of salbutamol sulphate.

According to a second aspect of the present invention there is provided a pharmaceutical composition consisting essentially of:
a propellant component consisting essentially of 1,1-difluoroethane (R-152a),
a surfactant component comprising at least one surfactant compound other than oleic acid; and
a drug component consisting of salbutamol sulphate.

The pharmaceutical compositions of the first and second aspects of the present invention are suitable for delivery from a pressured container, e.g. using a metered dose inhaler (MDI).

DETAILED DESCRIPTION

The pharmaceutical compositions of the first and second aspects of the present invention typically comprise from 0.01 to 1.0 weight % of the drug component, from 96.5 to 99.94 weight % of the propellant component and from 0.05 to 2.5 weight % of the surfactant component. Preferred compositions comprise from 0.05 to 0.5 weight % of the drug component, from 97.5 to 99.85 weight % of the propellant component and from 0.1 to 2.0 weight % of the surfactant component. Particularly preferred pharmaceutical compositions comprise from 0.07 to 0.2 weight % of the drug component, from 98.8 to 99.73 weight % of the propellant component and from 0.2 to 1.0 weight % of the surfactant component. All percentages are based on the total weight of the pharmaceutical compositions.

The propellant component in the pharmaceutical compositions of the first and second aspects of the present invention consists essentially of 1,1-difluoroethane (R-152a). Thus, we do not exclude the possibility that the propellant component may include small amounts of propellant compounds in addition to the R-152a. For example, the propellant component may additionally comprise one or more additional hydrofluorocarbon or hydrocarbon propellant compounds, e.g. selected from R-227ea, R-134a, difluoromethane (R-32), propane, butane, isobutane and dimethyl ether. If an additional propellant compound is included, the R-152a will constitute at least 90 weight %, e.g. from 90 to 99 weight % of the propellant component. Preferably, the R-152a will constitute at least 95 weight %, e.g. from 95 to 99 weight %, and more preferably at least 99 weight % of the propellant component. In an especially preferred embodiment, the propellant component is entirely R-152a, so that the pharmaceutical compositions of the invention comprise R-152a as the sole propellant.

The surfactant component in the pharmaceutical compositions of the first and second aspects of the present invention comprises at least one surfactant compound other than oleic acid. The surfactant component can assist dispersion of the solid drug particles in the propellant. Suitable surfactants include ethyl oleate, polyvinylpyrrolidone, sorbitan monooleate, sorbitan trioleate, isopropyl myristate, polyethylene glycols such as PEG 300, polyoxyethylene 20 sorbitan monooleate and monolaurate, propoxylated polyethyleneglycol and lecithin. The preferred surfactant is polyvinylpyrrolidone.

Preferably, the surfactant component consists essentially of at least one surfactant compound other than oleic acid and more preferably consists entirely of at least one surfactant compound other than oleic acid. Thus, in a preferred embodiment, the pharmaceutical compositions of the first and second aspects of the present invention are free of oleic acid.

By the terms "consists of" and "consisting of" as used herein, we are intending to exclude the presence of additional components. Thus, the drug component in the pharmaceutical compositions of the present invention consists entirely of salbutamol sulphate, so that the only drug in the pharmaceutical compositions is salbutamol sulphate. The salbutamol sulphate does not dissolve or dissolve significantly in the propellant component but forms a dispersion or suspension in the propellant/surfactant mixture. The suspended drug particles preferably have a diameter of less than 100 microns.

The pharmaceutical composition of the first aspect of the present invention is free of polar excipients. Polar excipients, such as ethanol, are used routinely in pharmaceutical compositions for treating respiratory disorders that are delivered using metered dose inhalers (MDIs). They are also referred to as solvents, co-solvents, carrier solvents and adjuvants. Their inclusion can serve to solubilise the surfactant or the drug in the propellant and/or inhibit deposition of drug particles on the surfaces of the metered dose inhaler that are contacted by the pharmaceutical composition as it passes from the container in which it is stored to the nozzle outlet. They are also used as bulking agents in two-stage filling processes where the drug is mixed with a suitable polar excipient. The most commonly used polar excipient is ethanol.

The present inventors have discovered that for salbutamol sulphate, the use of R-152a as the propellant reduces the need for polar excipients and allows compositions that contain very small amounts of polar excipients or that are free of polar excipients altogether to be prepared that still deliver good performance when delivered from a medication delivery device, such as a metered dose inhaler (MDI).

The pharmaceutical composition of the first aspect of the present invention preferably consists essentially of and more preferably consists entirely of the three listed components. By the term "consists essentially of", we mean that at least 95 weight %, more preferably at least 98 weight % and especially at least 99 weight % of the pharmaceutical composition consists of the three listed components.

The pharmaceutical composition of the second aspect of the present invention consists essentially of and preferably consists entirely of the three listed components. By the term "consists essentially of", we mean that at least 95 weight %, more preferably at least 98 weight % and especially at least 99 weight % of the pharmaceutical composition consists of the three listed components.

Although not preferred, the pharmaceutical composition of the second aspect of the present invention optionally contains at least one polar excipient. In principal, any polar material that is pharmaceutically acceptable may be employed as a polar excipient. Examples of suitable polar excipients include alcohols, such as ethyl alcohol (ethanol) and glycerol, and glycols, such as propylene glycol, polyethylene glycols and polypropylene glycols. The most preferred polar excipient is ethanol, which may be used together with other polar excipients but is preferably used alone. Preferably, the pharmaceutical composition of the second aspect of the present invention is free of any polar excipients such as ethanol.

Where a polar excipient is employed, the mandatory and preferred amounts of R-152a in the propellant component are as discussed above. Preferably, the propellant component will consist entirely of R-152a and the surfactant component will consist entirely of one or more surfactant compounds other than oleic acid even when a polar excipient is present.

The pharmaceutical compositions of the first and second aspects of the present invention find particular utility in the delivery of salbutamol sulphate from a pressurised aerosol container using a metered dose inhaler (MDI). In this application, the propellant component functions to deliver the drug as a fine aerosol spray.

In an especially preferred embodiment, the present invention provides a pharmaceutical composition for delivery from a pressurized container that is free of polar excipients comprising:
  a propellant component consisting of 1,1-difluoroethane (R-152a);
  a surfactant component consisting of at least one surfactant compound other than oleic acid; and
  a drug component consisting of salbutamol sulphate.

In this especially preferred embodiment, the pharmaceutical composition preferably consists essentially of and more preferably consists entirely of the three listed components. The surfactant component is preferably polyvinylpyrrolidone.

The pharmaceutical compositions of the invention may also comprise one or more other additives of the type that are conventionally used in drug formulations for pressurised MDIs, such as valve lubricants. Where other additives are included in the pharmaceutical compositions, they are normally used in amounts that are conventional in the art.

The pharmaceutical compositions of the invention are normally stored in pressurised containers or canisters which are to be used in association with a medication delivery device. When so stored, the pharmaceutical compositions are normally in the liquid state. In a preferred embodiment, the pressurised container is designed for use in a metered dose inhaler (MDI).

Accordingly, a third aspect of the present invention provides pressurised containers holding respectively the pharmaceutical compositions of the first and second aspects of the present invention. In a fourth aspect, the present invention provides medication delivery devices, especially metered dose inhalers, having pressurised containers respectively holding the pharmaceutical compositions of the first and second aspects of the present invention.

In an especially preferred embodiment, the present invention provides a pressurised container holding a pharmaceutical composition that is free of polar excipients comprising:
  a propellant component consisting of 1,1-difluoroethane (R-152a);
  a surfactant component consisting of at least one surfactant compound other than oleic acid; and
  a drug component consisting of salbutamol sulphate.

In another especially preferred embodiment, the present invention provides a medication delivery device, especially a metered dose inhaler, having a pressurised container holding a pharmaceutical composition that is free of polar excipients comprising:
  a propellant component consisting of 1,1-difluoroethane (R-152a);
  a surfactant component consisting of at least one surfactant compound other than oleic acid; and
  a drug component consisting of salbutamol sulphate.

In these especially preferred embodiments, the pharmaceutical composition preferably consists essentially of and more preferably consists entirely of the three listed components. The surfactant component is preferably polyvinylpyrrolidone.

The typical and preferred proportions of the drug component, propellant component and surfactant component in the pharmaceutical composition of these especially preferred embodiments are as discussed above.

The pharmaceutical compositions of the present invention are for use in medicine for treating a patient suffering or likely to suffer from a respiratory disorder and especially asthma.

Accordingly, the present invention also provides a method for treating a patient suffering or likely to suffer from a respiratory disorder, especially asthma, which comprises administering to the patient a therapeutically or prophylactically effective amount of a pharmaceutical composition as discussed above. The pharmaceutical composition is preferably delivered to the patient using a MDI.

The pharmaceutical compositions of the invention can be prepared by a simple blending operation in which the R-152a-containing propellant component, the surfactant component, and the salbutamol sulphate are mixed together in the required proportions in a suitable mixing vessel. Mixing can be promoted by stirring as is common in the art. Conveniently, the R-152a-containing propellant component is liquefied to aid mixing. If the pharmaceutical composition is made in a separate mixing vessel, it can then be transferred to pressurised containers for storage, such as pressurised containers that are used as part of medication delivery devices and especially MDIs.

The pharmaceutical compositions of the invention can also be prepared within the confines of a pressurised container, such as an aerosol canister or vial, from which the compositions are ultimately released as an aerosol spray using a medication delivery device, such as a MDI. In this method, a weighed amount of the salbutamol sulphate is introduced into the open container. A valve is then crimped onto the container and the 152a-containing propellant component, in liquid form, introduced through the valve into the container under pressure, optionally after first evacuating the container through the valve. The surfactant component can be mixed with the salbutamol sulphate or, alternatively, introduced into the container after the valve has been fitted, either alone or as a premix with the propellant component.

The whole mixture can then be treated to disperse the drug in the propellant or propellant/surfactant mixture, e.g. by vigorous shaking or using an ultrasonic bath. Suitable canisters may be made of plastics, metal or glass.

The canister may be filled with enough of the pharmaceutical composition to provide for a plurality of dosages. The pressurized aerosol canisters that are used in MDIs, typically contain 50 to 150 individual dosages.

For pharmaceutical compositions that comprise a drug in suspension in a propellant, the problem can arise that the suspended drug particles deposit on the interior surfaces of the canister and the valve of the drug delivery device. This problem can necessitate providing the canister interior with a special lining or coating, such as a fluoropolymer coating, and making the valves from specialist polymer materials. However, the pharmaceutical compositions of the invention are capable of forming a stable dispersion of the drug, thereby avoiding the problem of drug deposition, and yet deliver the drug as a sufficiently fine aerosol mist that is able to deliver the drug deep into the lung.

The present invention is now illustrated but not limited by the following examples.

Example 1

The solubility of various surfactants in R-134a and R-152a was investigated. The solubility was investigated by adding an excess of the surfactant (around 2 grams) to 200 g of the liquid propellant in a pressurised vessel. The vessel was equilibrated at 20° C. for a period of a few hours before decanting a weighed sample of the saturated supernatant liquid propellant through a filter into a clean vessel. The propellant was slowly removed by evaporation and the residue taken up in a small quantity of dichloromethane. The dichloromethane containing the dissolved residue was transferred to a weighed platinum crucible and heated (up to around 100° C.) to remove the solvent. The weighed, solvent-free residue represented the quantity of dissolved surfactant in the propellant. The results are shown in Table 1 below.

TABLE 1

| Surfactant | Refrigerant | Observation | NVR result |
|---|---|---|---|
| None | 152a | None | N/D |
| Tween | 152a | Sank to the bottom some dispersed in 152a | 0.6% |
| Tween | 134a | Floated on top coated the sides of the vessel some dispersed into the K134a | 0.25% |
| Span 80 | 152a | Sunk to the bottom Dispersed into the 152a | 0.22% |
| Span 80 | 134a | Floated on top and some left in bottom | 0.07% |
| Polyvinyl-pyrrolidone | 152a | Sunk to the bottom stayed in original form | 0.01% |
| Polyvinyl-pyrrolidone | 134a | Floated on top formed a hard brittle layer | 0.005% |
| Peg 400 | 152a | NO layers observed possible dispersed into 152a | 1.18% |
| Peg 400 | 134a | NO layers observed possible dispersed into 152a | 1.08% |

It is evident from the table above that PVP, Tween and Span all show significant increases in solubility in R-152a in comparison with R134a. Whilst PEG400 also shows some solubility increase, it is not as pronounced.

What is claimed is:

1. A pharmaceutical composition that is free of polar excipients, said composition comprising:

(a) a propellant component consisting essentially of 1,1-difluoroethane (R-152a) propellant, (b) a surfactant component consisting essentially of polyvinylpyrrolidone surfactant; and (c) a drug component consisting of solid drug particles of salbutamol sulphate, wherein the 1,1-difluoroethane propellant and polyvinylpyrrolidone surfactant provide a propellant/surfactant mixture in which the solid drug particles of salbutamol sulphate are suspended, and wherein the salbutamol sulphate and the polyvinylpyrrolidone are included in the mixture with the propellant as separate components.

2. The pharmaceutical composition of claim 1 which consists essentially of components (a), (b) and (c).

3. A pharmaceutical composition for delivery from a pressurised container, said composition consisting essentially of:

(a) a propellant component consisting essentially of 1,1-difluoroethane (R-152a) propellant, (b) a surfactant component consisting essentially of polyvinylpyrrolidone surfactant; and (c) a drug component consisting of solid drug particles of salbutamol sulphate, wherein the 1,1-difluoroethane propellant and polyvinylpyrrolidone surfactant provide a propellant/surfactant mixture in which the solid drug particles of salbutamol sulphate are suspended, and wherein the salbutamol sulphate and the polyvinylpyrrolidone are included in the mixture with the propellant as separate components.

4. The pharmaceutical composition of claim 1 which consists entirely of components (a), (b) and (c).

5. The pharmaceutical composition of claim 1, wherein the propellant component consists entirely of 1,1-difluoroethane (R-152a).

6. A sealed container that contains a pharmaceutical composition as claimed in claim 1.

7. The sealed container of claim 6 which is a pressurized container for use with a metered dose inhaler (MDI).

8. A metered dose inhaler (MDI) fitted with a pressurized container as claimed in claim 7.

9. A method for treating a patient suffering or likely to suffer from a respiratory disorder which comprises administering to the patient a therapeutically or prophylactically effective amount of a pharmaceutical composition as claimed in claim 1.

10. The method of claim 9, wherein the respiratory disorder is asthma.

11. The method of claim 9, wherein the pharmaceutical composition is delivered to the patient using a metered dose inhaler (MDI).

12. The pharmaceutical composition of claim 3 which consists entirely of components (a), (b) and (c).

13. The pharmaceutical composition of claim 12, wherein the propellant component consists entirely of 1,1-difluoroethane (R-152a).

14. The pharmaceutical composition of claim 2, wherein the propellant component consists entirely of 1,1-difluoroethane (R-152a).

15. The pharmaceutical composition of claim 3, wherein the propellant component consists entirely of 1,1-difluoroethane (R-152a).

16. The pharmaceutical composition of claim 4, wherein the propellant component consists entirely of 1,1-difluoroethane (R-152a).

17. The pharmaceutical composition of claim 1 comprising from 0.01 to 1.0 weight % of the drug component, from 96.5 to 99.94 weight % of the propellant component and from 0.05 to 2.5 weight % of the surfactant component.

18. The pharmaceutical composition of claim 2 consisting essentially of from 0.01 to 1.0 weight % of the drug component, from 96.5 to 99.94 weight % of the propellant component and from 0.05 to 2.5 weight % of the surfactant component.

19. The pharmaceutical composition of claim 3 consisting essentially of from 0.01 to 1.0 weight % of the drug component, from 96.5 to 99.94 weight % of the propellant component and from 0.05 to 2.5 weight % of the surfactant component.

20. The pharmaceutical composition of claim 4 consisting of from 0.01 to 1.0 weight % of the drug component, from 96.5 to 99.94 weight % of the propellant component and from 0.05 to 2.5 weight % of the surfactant component.

21. The pharmaceutical composition of claim 5 comprising from 0.01 to 1.0 weight % of the drug component, from 96.5 to 99.94 weight % of the propellant component and from 0.05 to 2.5 weight % of the surfactant component.

22. The pharmaceutical composition of claim 1 further comprising a valve lubricant.

23. The pharmaceutical composition of claim 1 which has been prepared: (i) by mixing the propellant component, the surfactant component, and the salbutamol sulphate together in the required proportions in a suitable mixing vessel, or (ii) by introducing a weighed amount of the salbutamol sulphate into an open container, fitting a valve device onto the container, introducing the propellant component, in liquid form, through the valve into the container under pressure and introducing the surfactant component, either alone or as a premix with the propellant, through the valve into the container under pressure, or (iii) by introducing a weighed amount of the salbutamol sulphate into an open container, introducing the surfactant component into the container, fitting a valve device onto the container, and introducing the propellant component, in liquid form, through the valve into the container under pressure.

24. The pharmaceutical composition of claim 3 which has been prepared: (i) by mixing the propellant component, the surfactant component, and the salbutamol sulphate together in the required proportions in a suitable mixing vessel, or (ii) by introducing a weighed amount of the salbutamol sulphate into an open container, fitting a valve device onto the container, introducing the propellant component, in liquid form, through the valve into the container under pressure and introducing the surfactant component, either alone or as a premix with the propellant, through the valve into the container under pressure, or (iii) by introducing a weighed amount of the salbutamol sulphate into an open container, introducing the surfactant component into the container, fitting a valve device onto the container, and introducing the propellant component, in liquid form, through the valve into the container under pressure.

* * * * *